(12) United States Patent
Tseung et al.

(10) Patent No.: US 6,746,851 B1
(45) Date of Patent: Jun. 8, 2004

(54) METHOD FOR AUTOMATED STAINING OF SPECIMEN SLIDES

(75) Inventors: Ken K. Tseung, Fremont, CA (US); Glenn Takayama, Danville, CA (US); Norman K. Rhett, San Ramon, CA (US); Mark V. Corl, Fremont, CA (US)

(73) Assignee: Lab Vision Corporation, Fremont, CA (US)

( * ) Notice: Subject to any disclaimer, the term of this patent is extended or adjusted under 35 U.S.C. 154(b) by 0 days.

(21) Appl. No.: 09/483,248

(22) Filed: Jan. 14, 2000

(51) Int. Cl.[7] .................................................. G01N 1/30
(52) U.S. Cl. ................................... 435/40.5; 435/40.52
(58) Field of Search ........................... 455/283.1, 286.1, 455/287.1, 40.5, 40.52; 356/246; 422/58, 62, 63, 67; 436/43

(56) References Cited

U.S. PATENT DOCUMENTS

| | | | | |
|---|---|---|---|---|
| 5,439,649 A | * | 8/1995 | Tseung et al. | |
| 5,573,727 A | | 11/1996 | Keefe | 422/63 |
| 5,595,707 A | * | 1/1997 | Copeland et al. | |
| 5,650,327 A | * | 7/1997 | Copeland et al. | |
| 5,654,199 A | * | 8/1997 | Copeland et al. | 436/46 |
| 5,800,784 A | | 9/1998 | Horn | 422/101 |
| 5,839,091 A | * | 11/1998 | Rhett et al. | 702/19 |
| 5,919,553 A | | 7/1999 | Kavanaugh | 428/195 |
| 5,948,359 A | * | 9/1999 | Kalra et al. | |
| 6,352,861 B1 | | 3/2002 | Copeland et al. | 436/46 |

FOREIGN PATENT DOCUMENTS

| | | | | |
|---|---|---|---|---|
| DE | 197 36 470 A1 | 4/1999 | ............ | G01N/1/28 |
| WO | PCT/US91/01149 | 2/1991 | | |
| WO | WO 92/01919 | 2/1992 | ............ | G01N/1/28 |

OTHER PUBLICATIONS

Tecan, SLT, Cavro, Progressing as One in Laboratory Automation.
Jung (2/91), Histostainer Ig.
BioGenex, OptiMax™ Automated Cell Staining System.
Biotex Solutions (1993), Techmate 500™ & Techmate 1000™ Automated Immunostaining System.
Sakura Finetek USA (1995), RSG–61 Hematology Slide Stainer.
Beckman, Biomek® 2000 Automated Workstation.
Ventana Medical Systems, Inc. (Mar. 31, 1994), In Situ Hybridization System.
Shandon, Inc. (9/94), Cadenza Automated Immunostainer.
Hamilton Company, Microlab® SPE.
Matrix Technologies Corp. (9/93), Automated Sample Handling.
Packard Instrument Co. (8/94), MultiPROBE® Robotic Liquid handling.
Rosys, Inc., Rosys Plato 3000.

\* cited by examiner

*Primary Examiner*—Ralph Gitomer
(74) *Attorney, Agent, or Firm*—Wood, Herron & Evans L.L.P.

(57) ABSTRACT

A method and apparatus for specimen slide (710) preparation is disclosed. The method and apparatus of the present invention uses slide trays (700) that have receptacles for at least one specimen slide (710) and an associated reagent pack (720). The specimen slide (710) and reagent pack (720) includes respective identifiers (420, 411) that specify a particular slide preparation protocol that should be followed. The method reads the identifiers (420, 411) on the reagent pack and the slide to verify that the correct slide preparation protocol is being used.

10 Claims, 18 Drawing Sheets

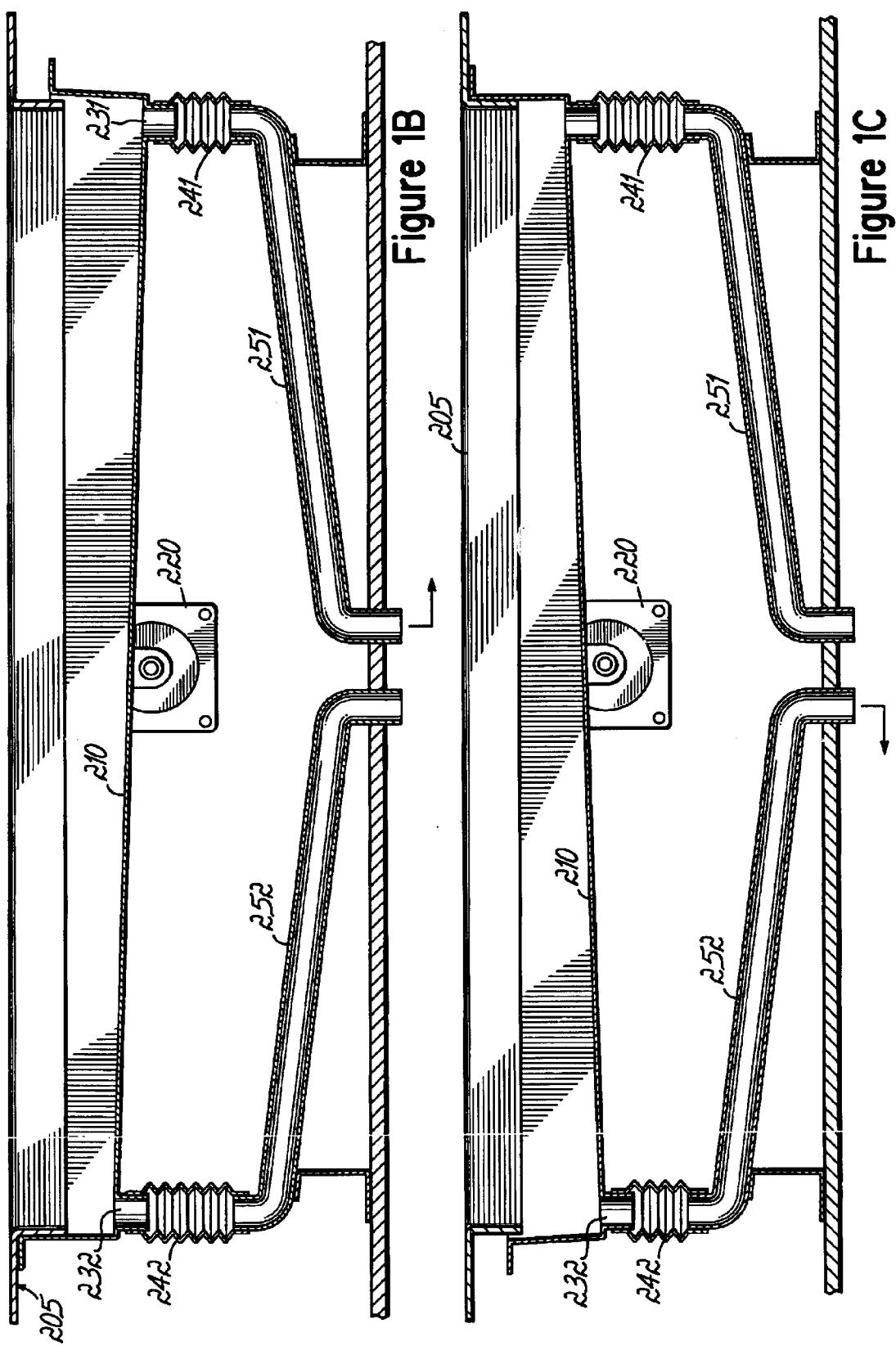

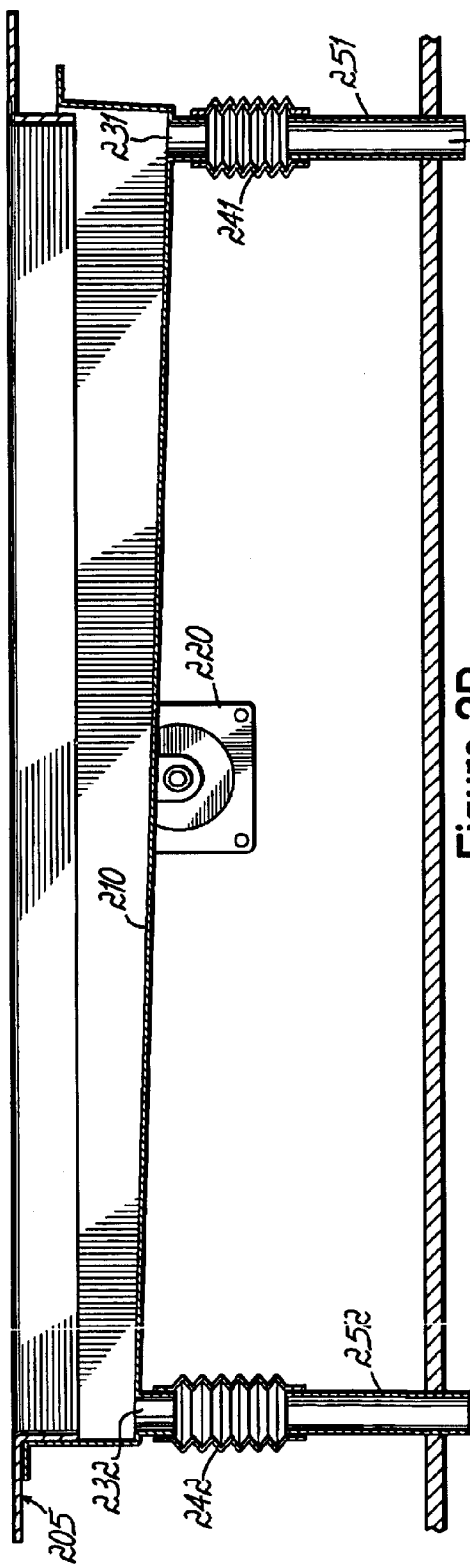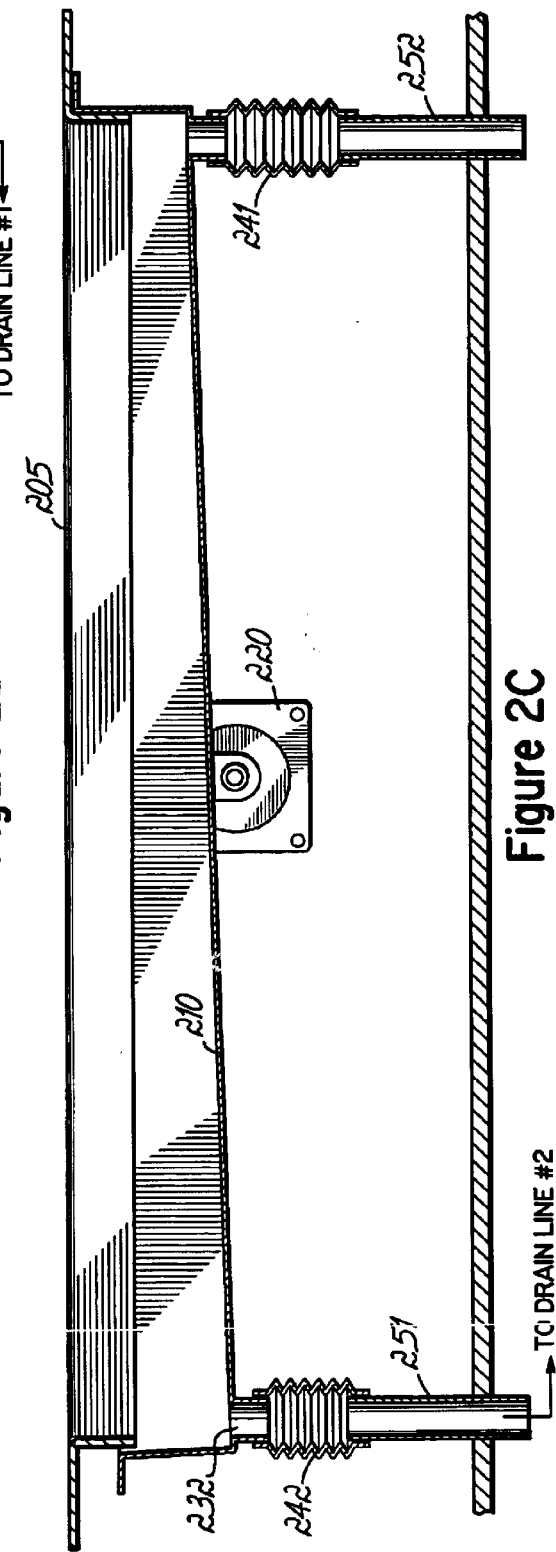
Figure 2B
Figure 2C

METHOD FOR AUTOMATED STAINING OF SPECIMEN SLIDES

FIELD OF THE INVENTION

The present invention relates to the field of medical lab equipment. In particular the present invention discloses a fully automated system for staining tissue specimens and cell preparations.

BACKGROUND OF THE INVENTION

A normal function of medical laboratories is to examine cells and cell tissue under a microscope. The lack of contrast between individual cells and the background matrix or between individual parts of cells can make it difficult to examine cell and tissue preparations. To improve the contrast, researchers have applied stains to cell and tissue specimens to be examined. The stains are absorbed differently by the various structures in cells such that the contrast between the different cell structures is improved.

Staining tissue specimens is a nontrivial time consuming process. Often a number of different staining and rinsing stages are required. Each stage requires a specific amount of reagent or buffer and takes a specific amount of time. Thus, trained technicians are often employed to perform such operations. Furthermore, hospitals and laboratories must stain very large numbers of tissue specimens for patient diagnoses. Thus, automated tissue staining systems have been developed. By automating the process, expensive human labor is eliminated. Furthermore, automatically staining specimens significantly reduces the probability of an error occurring during the staining process.

To ensure that the proper staining procedures are followed, most automatic staining systems require that the user carefully enter the staining protocol and load the proper reagents. The complicated procedures require user training before such devices can be operated effectively. It would therefore be desirable to simplify the operation of an automatic tissue-staining device.

SUMMARY OF THE INVENTION

A method and apparatus for specimen slide preparation is disclosed. The method and apparatus of the present invention uses slide trays that have receptacles for at least one specimen slide and an associated reagent pack. The specimen slide and/or reagent pack includes an identifier that specifies a particular slide preparation protocol that should be followed. The method and apparatus reads the identifier to determine the particular slide preparation protocol and then prepares the specimen slide according to the particular slide preparation protocol. The apparatus may obtain some or all of the reagents needed for the particular slide preparation protocol from the reagent pack.

Other objects feature and advantages of present invention will be apparent from the drawings and the detailed description that follows.

BRIEF DESCRIPTION OF THE DRAWINGS

The objects, features, and advantages of the present invention will be apparent to one skilled in the art, in view of the following detailed description in which:

FIG. 1B illustrates the tiltable sink assembly of FIG. 1A wherein the tiltable sink assembly is tilted to the right.

FIG. 1C illustrates the tiltable sink assembly of FIG. 1A wherein the tiltable sink assembly is tilted to the left.

FIG. 2B illustrates the tiltable sink assembly of FIG. 2A wherein the tiltable sink assembly is tilted to the right.

FIG. 2C illustrates the tiltable sink assembly of FIG. 2A wherein the tiltable sink assembly is tilted to the left.

DETAILED DESCRIPTION OF THE PREFERRED EMBODIMENT

A method and apparatus for automatically staining tissue specimens is disclosed. In the following description, for purposes of explanation, specific nomenclature is set forth to provide a thorough understanding of the present invention. However, it will be apparent to one skilled in the art that these specific details are not required in order to practice the present invention. For example, the present invention has been described with reference to staining of tissue specimens. However, the same techniques can easily be applied to other types of slide preparation work.

The Autostainer Hardware

The present invention comprises advances in automated slide staining. An example of an automatic slide staining apparatus can be found the first figure of U.S. Pat. No. 5,839,091, issued Nov. 17, 1998, and entitled "Method and apparatus for automatic tissue staining" which is hereby incorporated by reference in its entirety. An autostainer system is used for staining tissue specimens that are placed onto glass slides. The present invention uses several different slide racks wherein each slide rack holds one or more slides. In one embodiment, there are six slide racks and each slide rack is capable of holding four slides such that the autostainer can prepare twenty-four different slides simultaneously.

An autostainer uses a robotic delivery system that delivers bulk reagents, small supply reagents, buffer solutions, and air to the glass slides. The robotic delivery system is controlled by a computer system. The computer system executes an autostainer control program that sends control commands to control the robotic delivery system. In one embodiment, the robotic delivery system of the autostainer consists of an X-axis mechanism, a Y-axis mechanism, and a Z head as illustrated in U.S. Pat. No. 5,839,091. The Z head has a Bulk fluid dispensing tube for dispensing a few selected bulk reagents and buffer rinse solution, an air blade to blow air onto slides, and a syringe probe for picking up reagents that will be placed onto the glass slides.

To prevent contamination, the syringe probe is cleaned in a reagent probe wash bin between the uses of different reagents. The wash bin has three different receptacles that are used in three stages. The first hole is used to rinse the inside of the probe by forcing buffer rinse solution through the inside of probe and down into a first drain receptacle. The second receptacle is used to clean the outside of the probe by forcing buffer rinse solution through the inside of probe while the probe is in the tightly confined second receptacle such that the buffer solution is force upward on the outside of the probe. Finally, the probe is placed into a third receptacle and air is forced through the probe to clean out the buffer rinse solution.

Figure 1A:
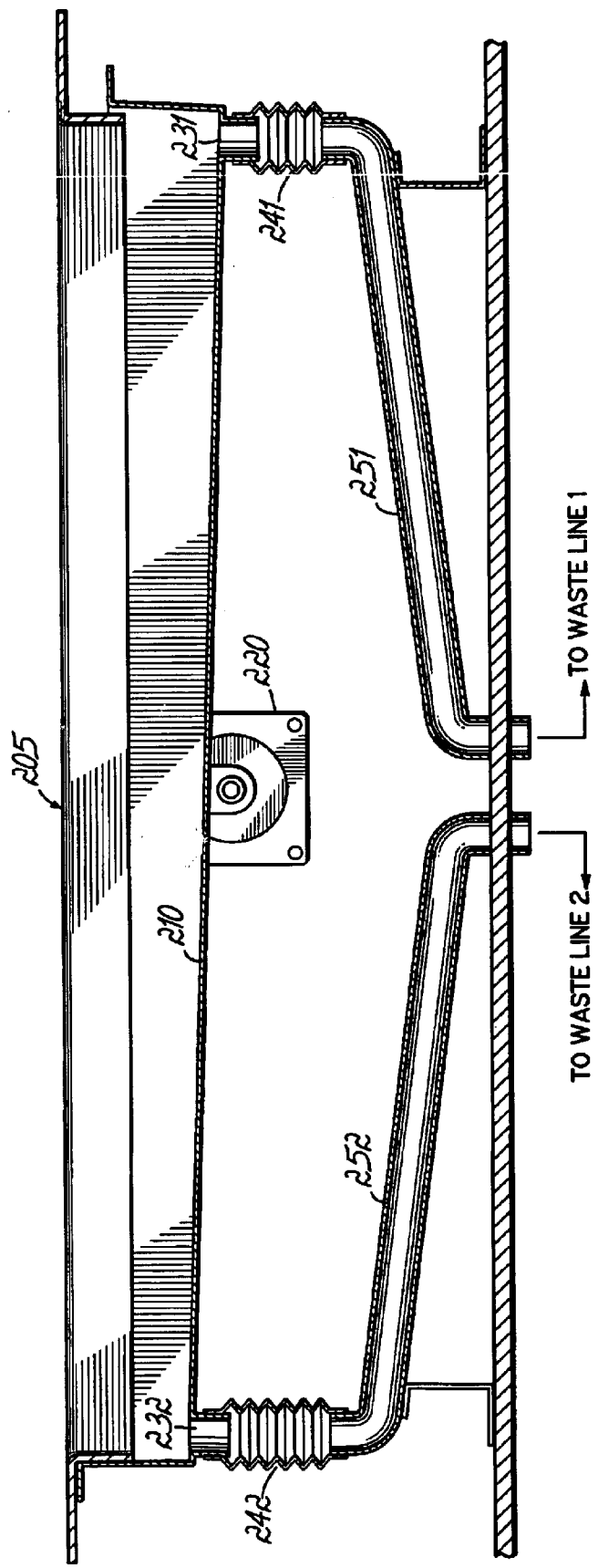
FIG. 1A illustrates a cut-away view of a first tiltable sink assembly embodiment.

Beneath the slide racks of the autostainer is a sink assembly. The sink assembly catches the reagents and buffer rinse solution that drip off the slides. FIG. 1A illustrates a cut-away top view of a first embodiment of a sink assembly. As illustrated in FIG. 1A, a tiltable sink 210 sits beneath a support bracket 205 for the slide racks (not shown). The tiltable sink 210 may be tilted left or right using a tilt mechanism 220. When the tiltable sink 210 is tilted down on the right side as illustrate in FIG. 1B, all the liquid waste spilling off the slides will drain out of drain hole 231 on the right side, through corrugated tubing 241 and drain pipe 251, and finally to a waste line #1 (not shown). Similarly, when the tiltable sink 210 is tilted down on the left side as illustrated in FIG. 1C, all the liquid waste will drain out of drain hole 232, through corrugated tubing 242 and drain pipe 252, and finally to a waste line #2 (not shown). As illustrated in FIGS. 1A through 1C, the two waste lines conveniently exit the device at the same location.

With the tiltable sink system of the present invention, the present invention can send different types of waste down different waste lines such that a first waste line may be used to remove nonhazardous waste and the other waste line may be used to remove hazardous waste. The non hazardous waste line may simply be connected to a sewage drain pipe. The hazardous waste line should be connected to hazardous waste container that is disposed of appropriately.

Figure 2A:
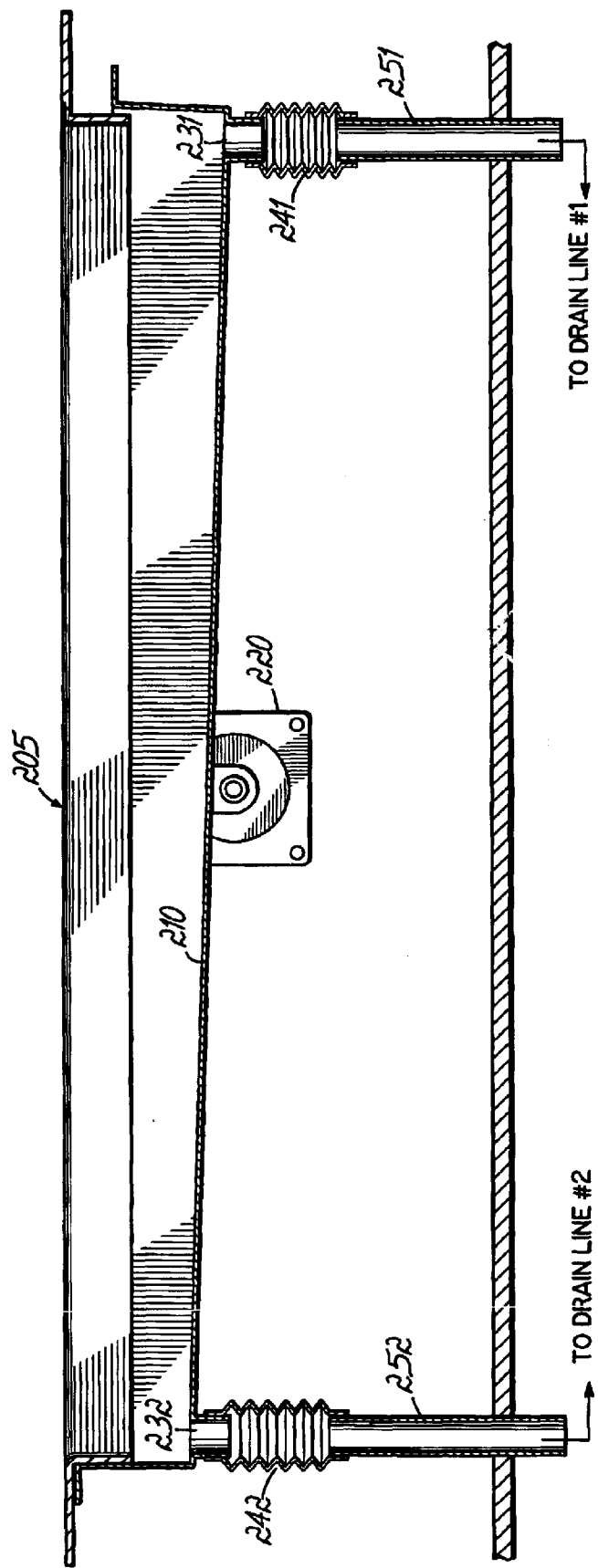
FIG. 2A illustrates a cut-away view of a second tiltable sink assembly embodiment.

FIGS. 2A through 2C illustrate an alternate embodiment of a tiltable sink system. Referring to FIGS. 2A through 2C, the drain line travels straight down such that the two waste lines exit at different locations.

Fluid Flow Components

Figure 3:
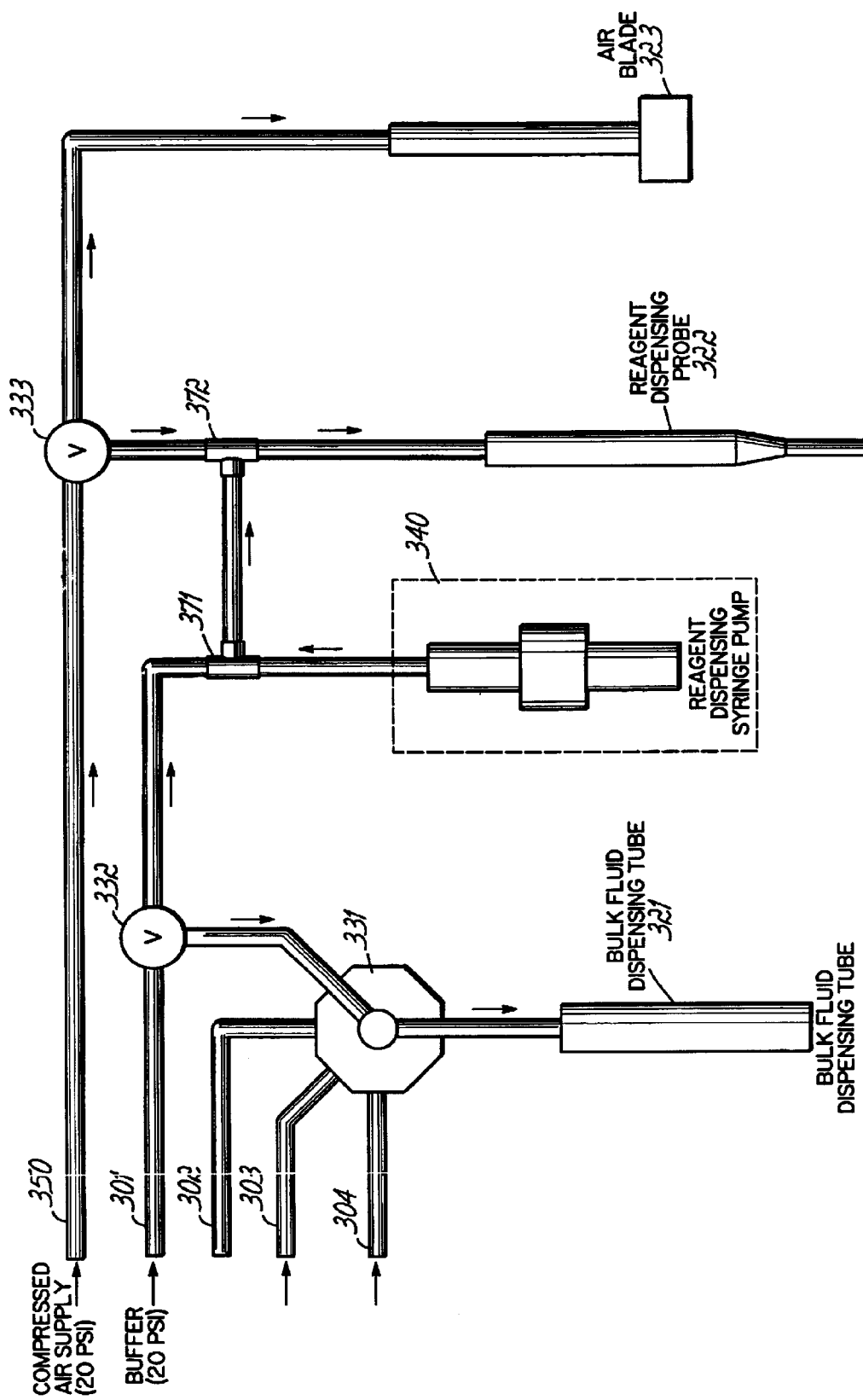
FIG. 3 illustrates a conceptual diagram of the internal fluid flow components of the autostainer apparatus.

Several other components are also located inside the autostainer. FIG. 3 illustrates a conceptual diagram of the fluid flow components of the autostainer. Referring to FIG. 3, three different output devices located on the Z-Head assembly of the autostainer deliver air or fluid to the slides.

A first output device is the bulk fluid dispensing tube 321. The bulk fluid dispensing tube 321 is used to deliver relatively large quantities of fluid to slides. The bulk fluid dispensing tube 321 may dispense buffer solution from buffer supply 301 or reagents from internal bulk reagent supplies 302, 303, and 304. The particular fluid dispensed is selected by 8-way distribution valve 331.

A second output device is the reagent-dispensing probe 322. The reagent-dispensing probe 322 draws in specific reagents using syringe pump 340 and then dispenses drawn-in reagents onto specific slides. To prevent contamination of the reagent-dispensing probe 322 from different reagents, the autostainer cleans the reagent-dispensing probe 322. Specifically, the autostainer first flushes the reagent dispensing probe 322 by forcing buffer solution through the reagent dispensing probe 322 using three-way valve 332. Then, the autostainer dries the reagent dispensing probe 322 by forcing air through the reagent dispensing probe 322 using three-way valve 333.

The third output device is air blade 323. Air blade 323 is used to dry off slides and blow away extra reagents.

Autostainer Reagent Packs

To simplify the operation, the present invention introduces an autostainer system with a greatly simplified operation. To use the autostainer system of the present invention, a user simply adds a set of slides where each slide is accompanied by a specific reagent pack that contains the reagents needed for a specific slide preparation protocol. The reagent pack further includes information that identifies the slide preparation protocol to be performed.

Figure 4A:
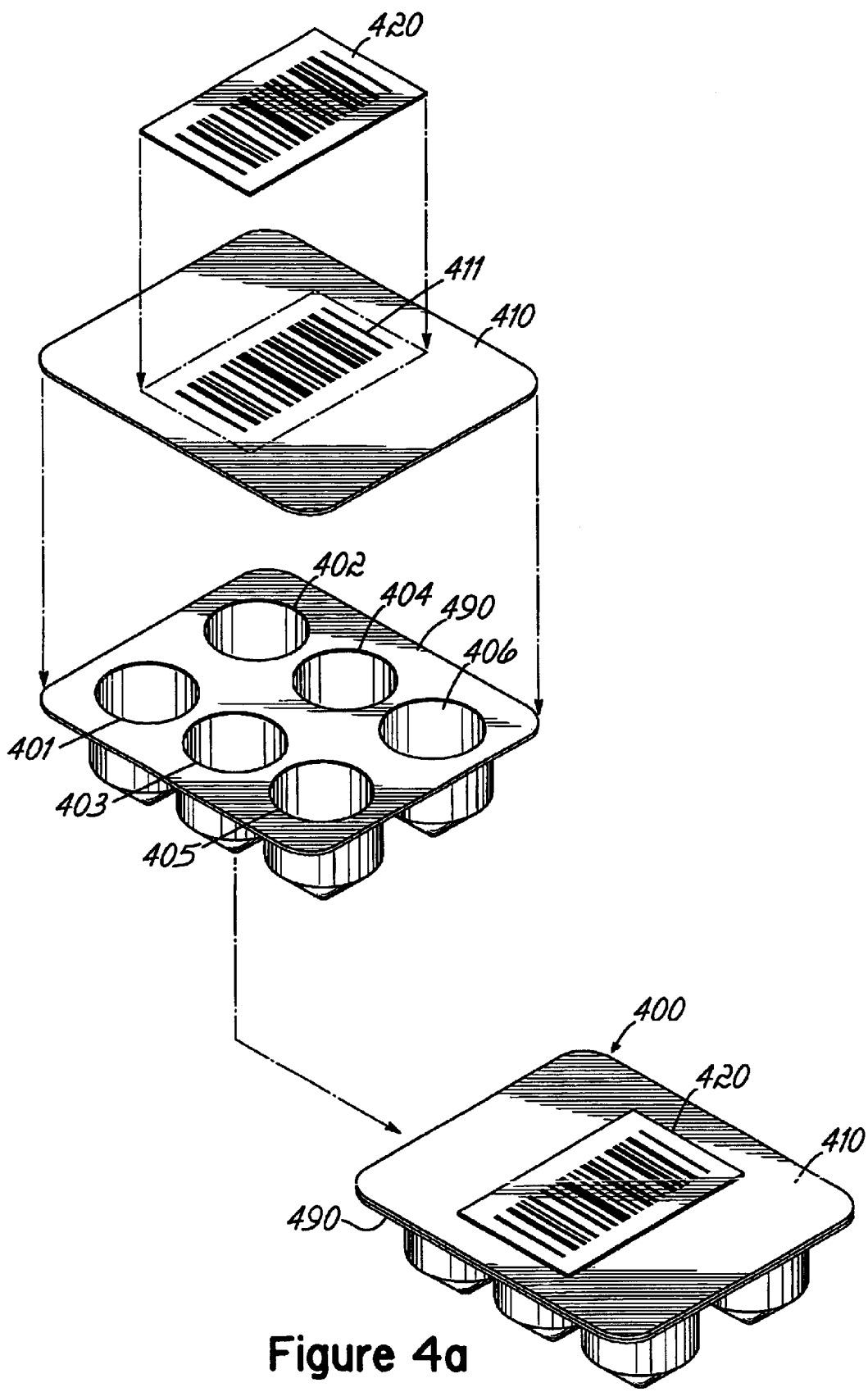
FIG. 4a illustrates a first arrangement of a reagent pack for the autostainer apparatus of the present invention.

FIG. 4a illustrates a first embodiment of a reagent pack that may be used with the autostainer system of the present invention. As illustrated in FIG. 4a, the reagent pack comprises a container with a set of wells (401 to 406 in FIG. 4a) for storing reagents. The container is sealed using a cover 410. The cover 410 may include an identification mark such as barcode 411 to identify the slide preparation protocol to be performed. The cover 410 protects and retains the reagents in the wells 401 to 406, yet the reagent dispensing probe 322 is able to puncture and access the reagents as needed.

Figure 7A:
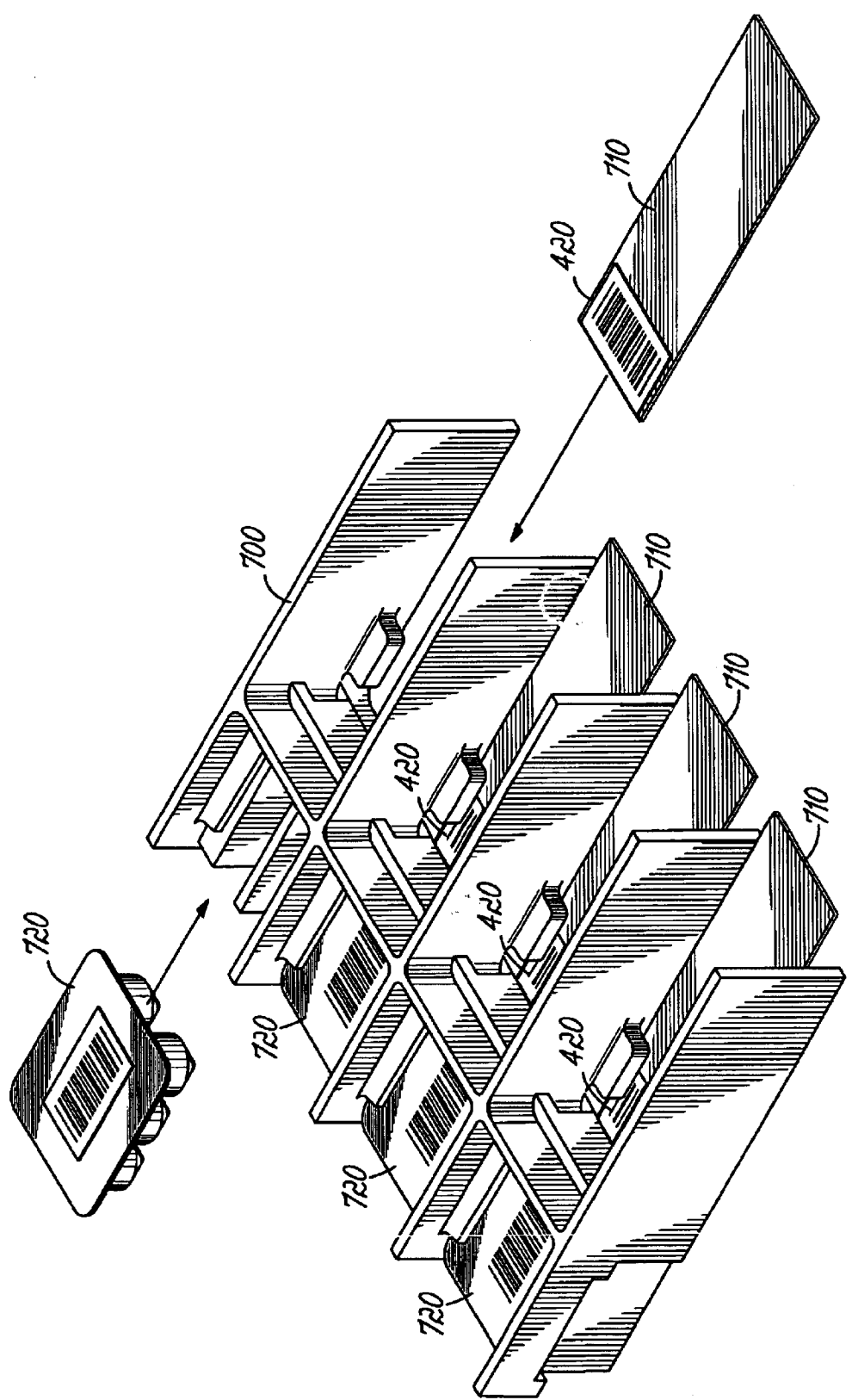
FIG. 7a illustrates a front view of a combined slide and reagent pack for preparing four slides.

The cover 410 may further include a second barcode identification sticker 420. As shown in FIG. 7a, the barcode identification sticker 420 can be placed directly onto a slide 710 to be performed such that the autostainer will automatically know the slide preparation protocol to be performed.

Figure 4B:
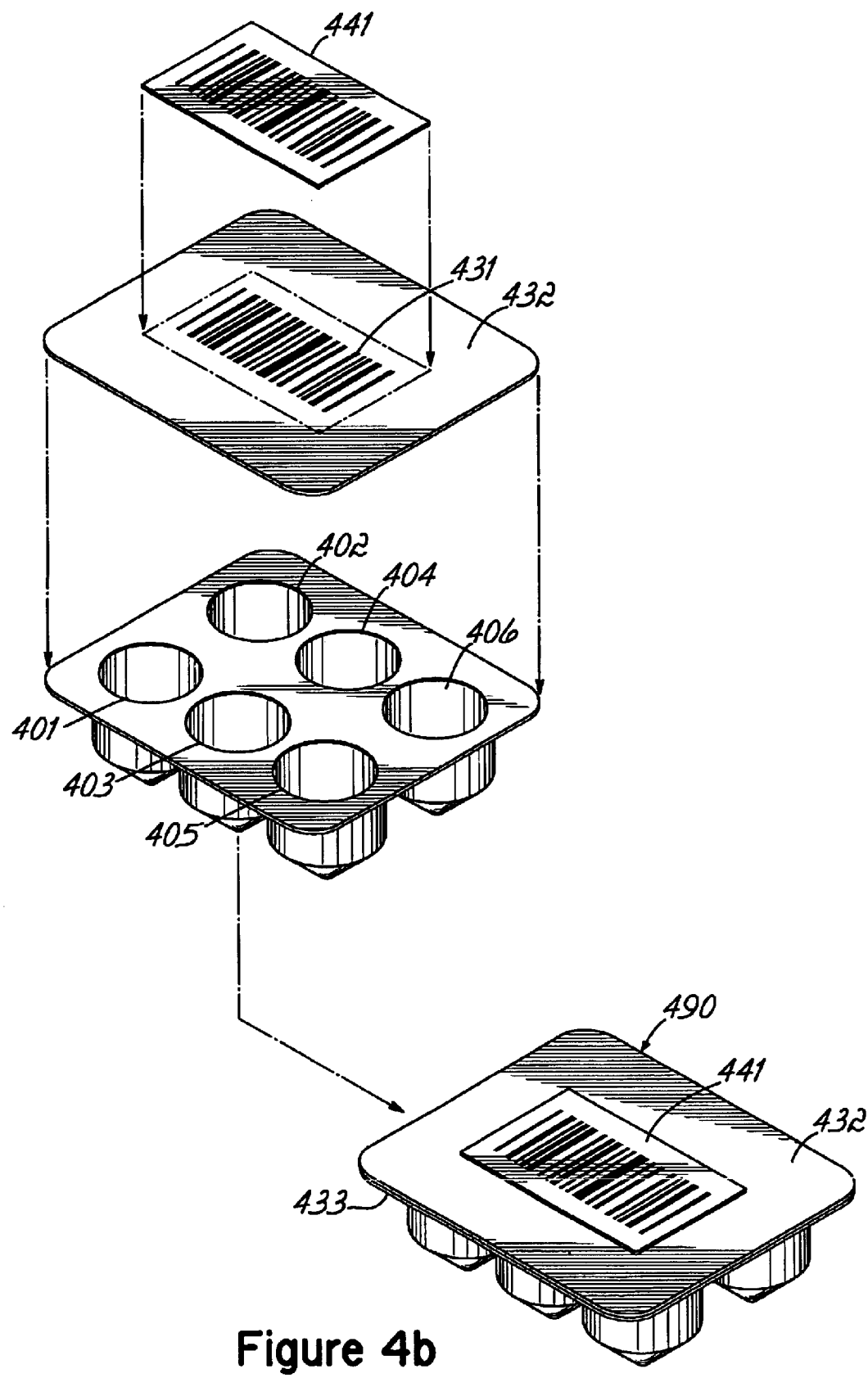
FIG. 4b illustrates a second arrangement of a reagent pack for the autostainer apparatus of the present invention.

FIG. 4b illustrates an alternate embodiment of a reagent pack 490. In the alternate embodiment of FIG. 4b, the identifiers 431 and 441 have been placed on a cover 432 parallel to the line of wells 401 to 406. In yet another embodiment (not shown), a tiltable sink is created with four drain holes with one hole at each corner. In such an embodiment, four different waste systems may be used.

Figure 5C:
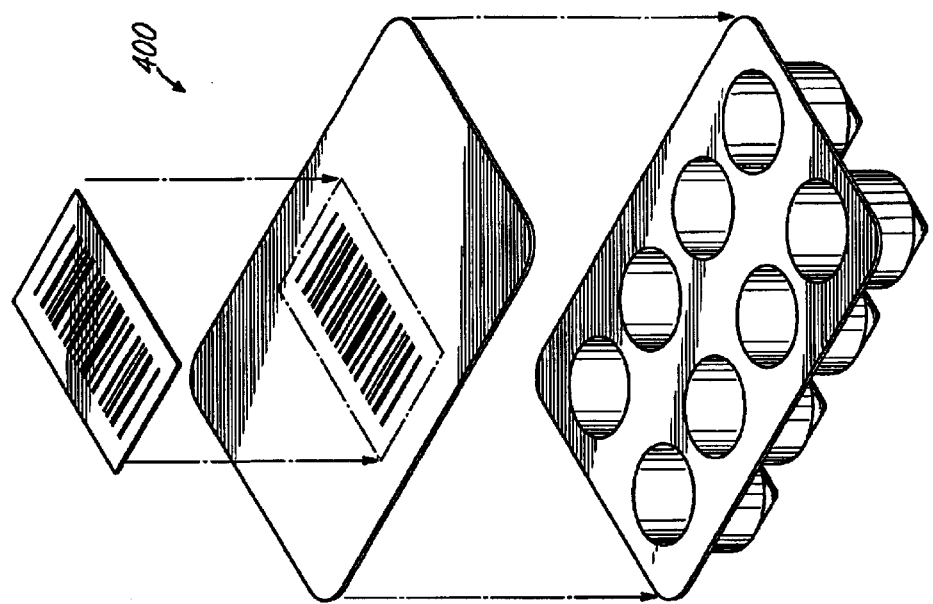
FIG. 5c illustrates an eight well reagent pack for the autostainer apparatus of the present invention.
Figure 5B:
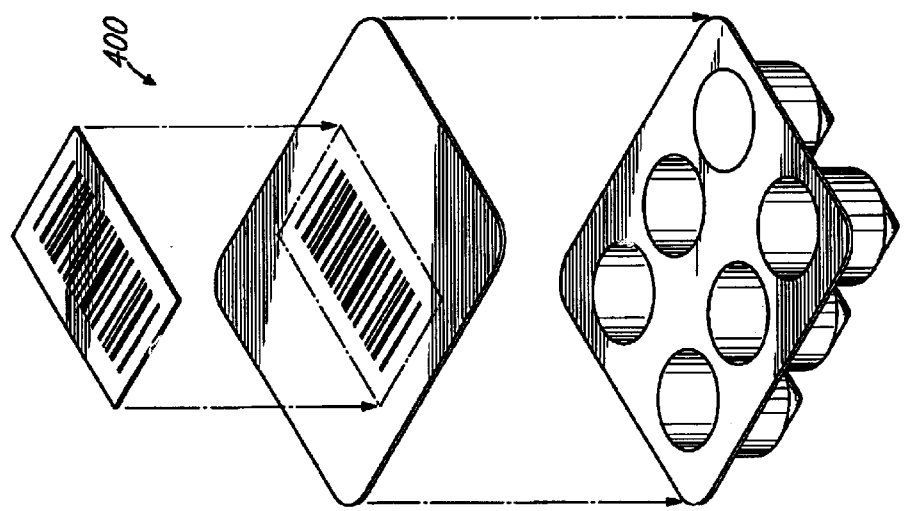
FIG. 5b illustrates a six well reagent pack for the autostainer apparatus of the present invention.
Figure 5A:
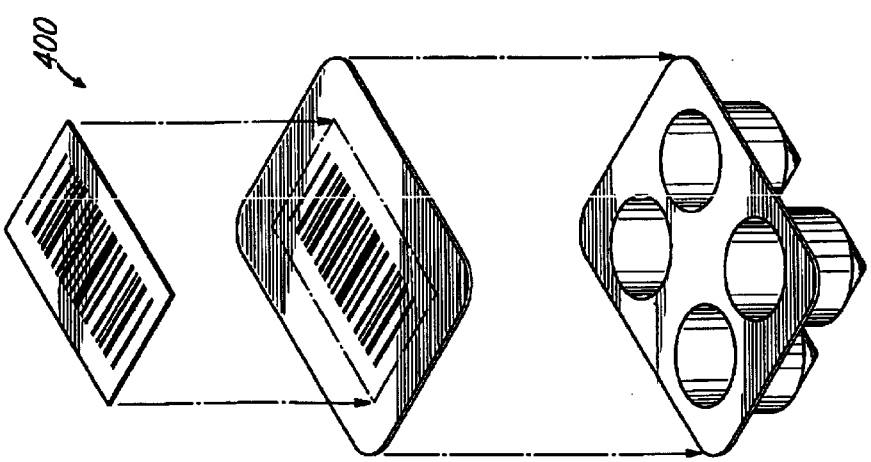
FIG. 5a illustrates a four well reagent pack for the autostainer apparatus of the present invention.

The autostainer system of the present invention is capable of handling many different slide preparation protocols that require different numbers of reagents. FIGS. 5a, 5b, and 5c illustrate different sized reagent packs for different protocols. FIG. 5a illustrates a simple four reagent pack for simple slide preparations. FIG. 5b illustrates the six-reagent pack of FIG. 4a. FIG. 5c illustrates an eight-reagent pack for complex slide preparation protocols.

Figure 6A:
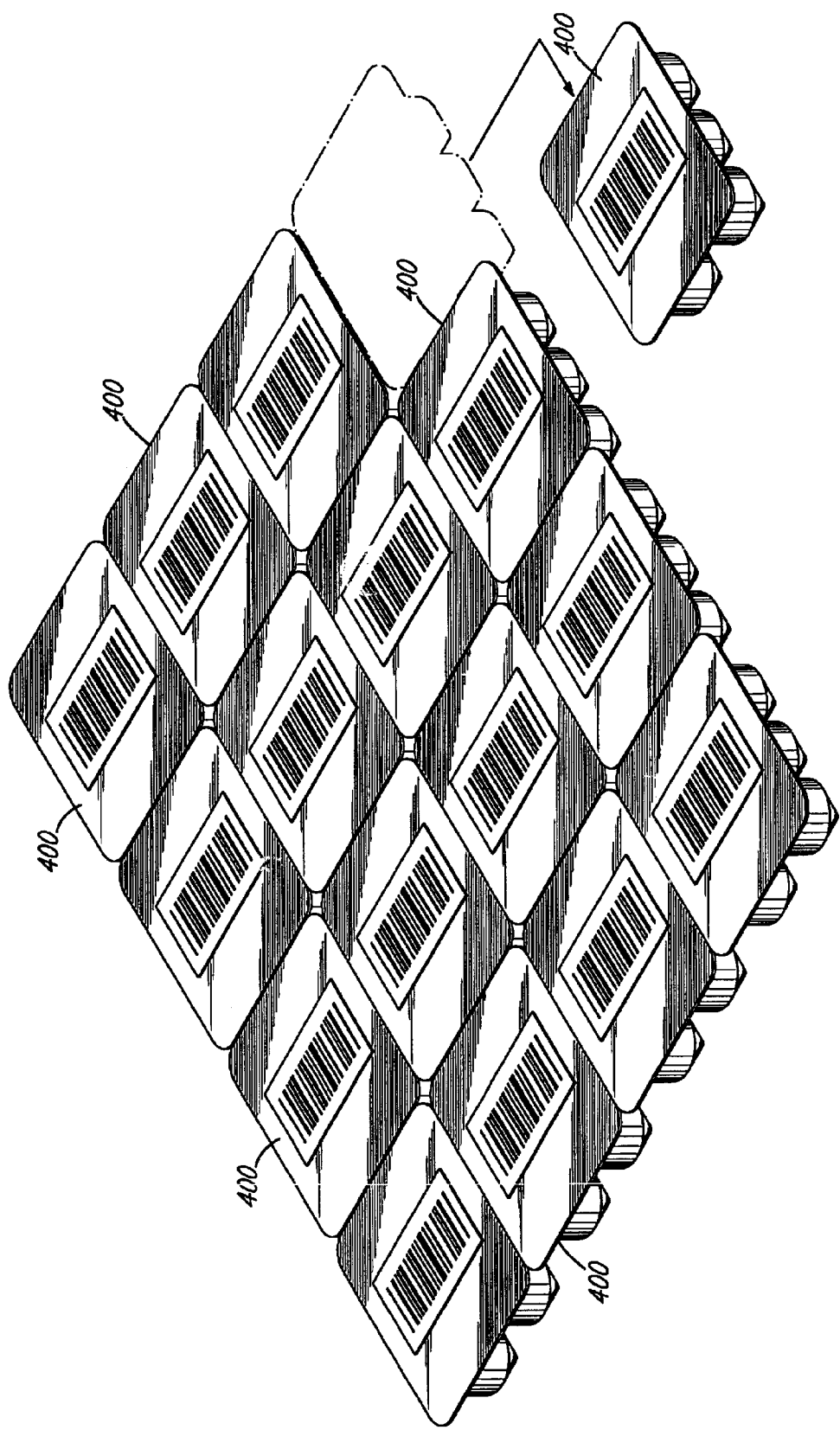
FIG. 6a illustrates a first embodiment of bulk packaged reagent packs.
Figure 6B:
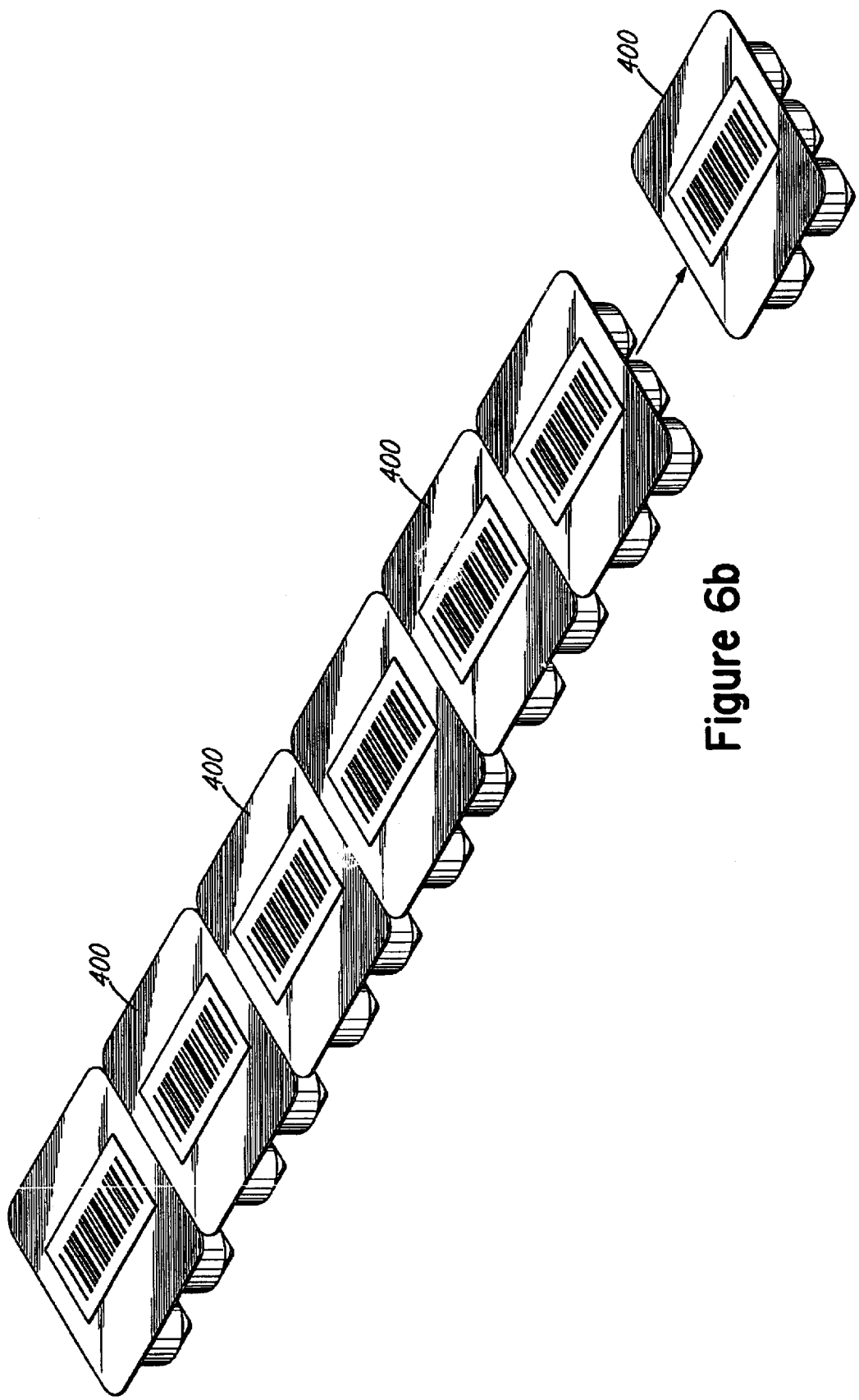
FIG. 6b illustrates a second embodiment of bulk packaged reagent packs.

The autostainer will be used to perform large numbers of slide preparations. Each slide preparation requires a reagent pack. To simplify purchasing, reagent packs may be purchased in bulk packages. FIG. 6a illustrates one possible bulk package where several reagent packs are sold in a perforated two-dimensional matrix of individual reagent packs. FIG. 6b illustrates an alternate bulk package where several reagent packs are sold as a strip of connected individual reagent packs.

Autostainer Slide Racks

Figure 7B:
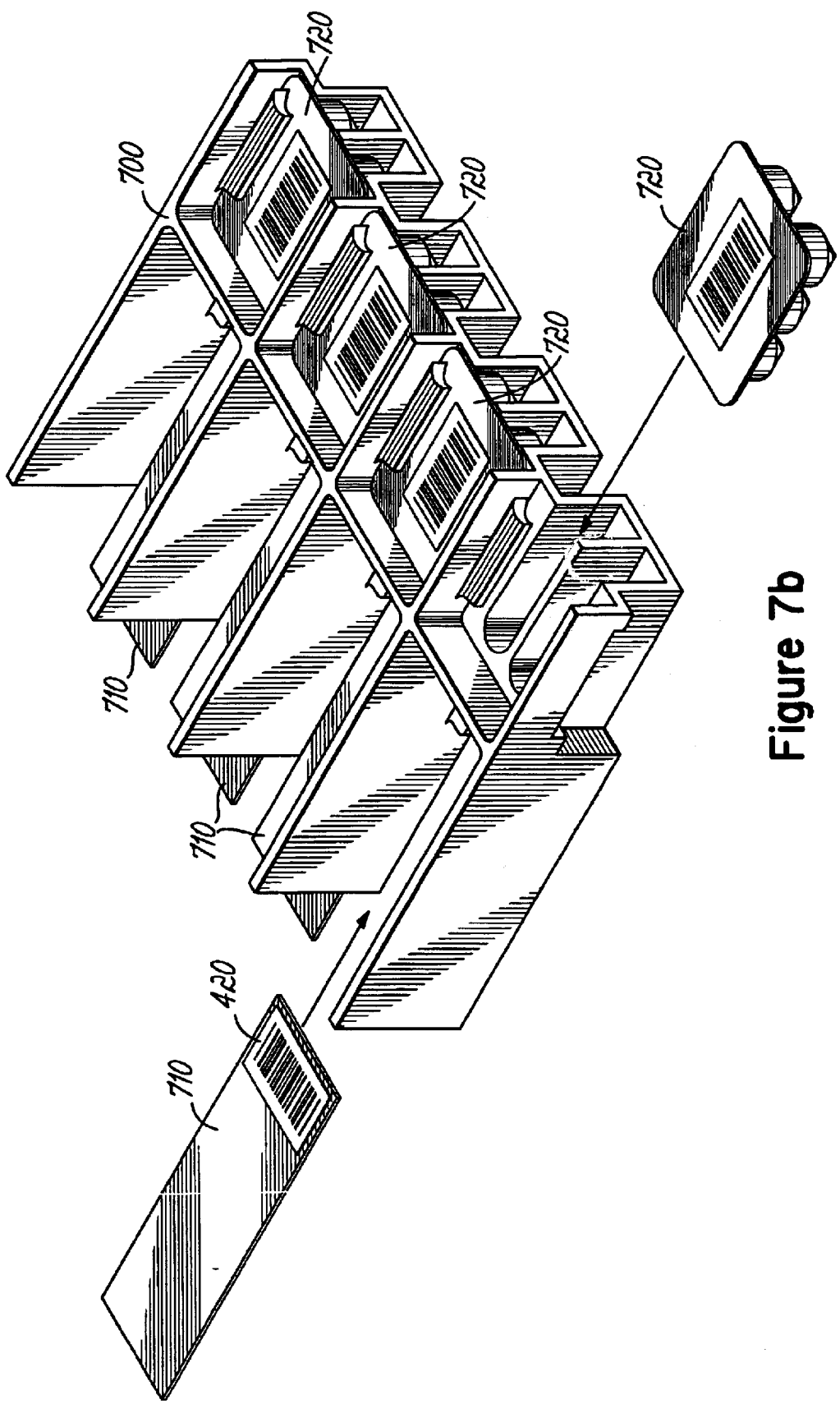
FIG. 7b illustrates a back view of a combined slide and reagent pack for preparing four slides.

The slide racks for the autostainer of the present invention have been designed for ease-of-use and maximum flexibility. FIG. 7a illustrates a front view of one possible slide rack that may be used in the autostainer of the present invention. The slide rack 700 has four slide positions such that the slide rack 700 can hold four slides 710. Other slide rack embodiments may hold more or less than four slides. The slides may be standard U.S. or international sized slides. The slide rack 700 further includes four reagent positions for storing reagent packs 720 associated with the adjacent slide positions. FIG. 7b illustrates a back view of the slide rack 700.

Autostainer Control and Programming

As stated in the previous section, the autostainer is controlled by a computer system. In a present embodiment, the computer system is based on a standard Personal Computer (PC) motherboard with a PCI bus. The computer system runs an autostainer control program to control the operation of the autostainer.

The autostainer control program is a sophisticated control program that implements many security, automatic slide protocol programming, control, and logging features. To fully describe the autostainer control program, this document will step through a sample use of the autostainer.

User Loading

To operate the autostainer, a user loads slide trays (as illustrated in FIGS. 7a and 7b) with slide specimens and associated reagent packs. In one embodiment, the user simply places the proper reagent pack in the reagent pack receptacle adjacent to the specimen slide to be prepared. In another embodiment, the user places an associated identifier on the frosted area of the specimen slide to be prepared. This can be done by peeling off a barcode sticker 420 from the reagent pack 400 and placing it on the frosted area of the slide. By specifically labeling each slide with the protocol to be performed, no error can be introduced by accidentally placing the wrong reagent pack next to a specimen slide.

Slide Preparation Protocol Identification

After loading one or more slide trays, the user places the loaded slide trays into the autostainer system. The user then instructs the autostainer system to commence slide preparation by activating a "restart" input. If the user has added very high priority slides to the autostainer, the user may instead press a "STAT" input to indicate that the new slides are very high priority. The autostainer system then commences operation by first examining the loaded slides and reagent packs to determine the slide preparation protocols that need to be performed. Specifically, the autostainer system reads all the identifiers (on the slides and/or reagent packs) and then consults a slide preparation protocol database that maps the different identifiers on the reagent packs with the slide preparation protocols to be performed.

The slide preparation protocol database may be periodically updated by shipping media such as floppy disks or CD-ROMs that are inserted into an appropriate drive on the autostainer. In one embodiment, the autostainer system uses a network to automatically retrieve database updates. This may be performed by having the autostainer coupled to a telephone line with a modem such that the autostainer automatically calls specific number to obtain slide preparation protocol database updates. In an alternate embodiment, the autostainer may be coupled to the global Internet such that the autostainer may connect to a server that stores the most recent slide preparation protocol database information. In any of these embodiments, the autostainer may also simultaneously receive program updates such that the software that controls the autostainer may be automatically updated.

Slide Staining Apparatus Operation

Figure 8A:
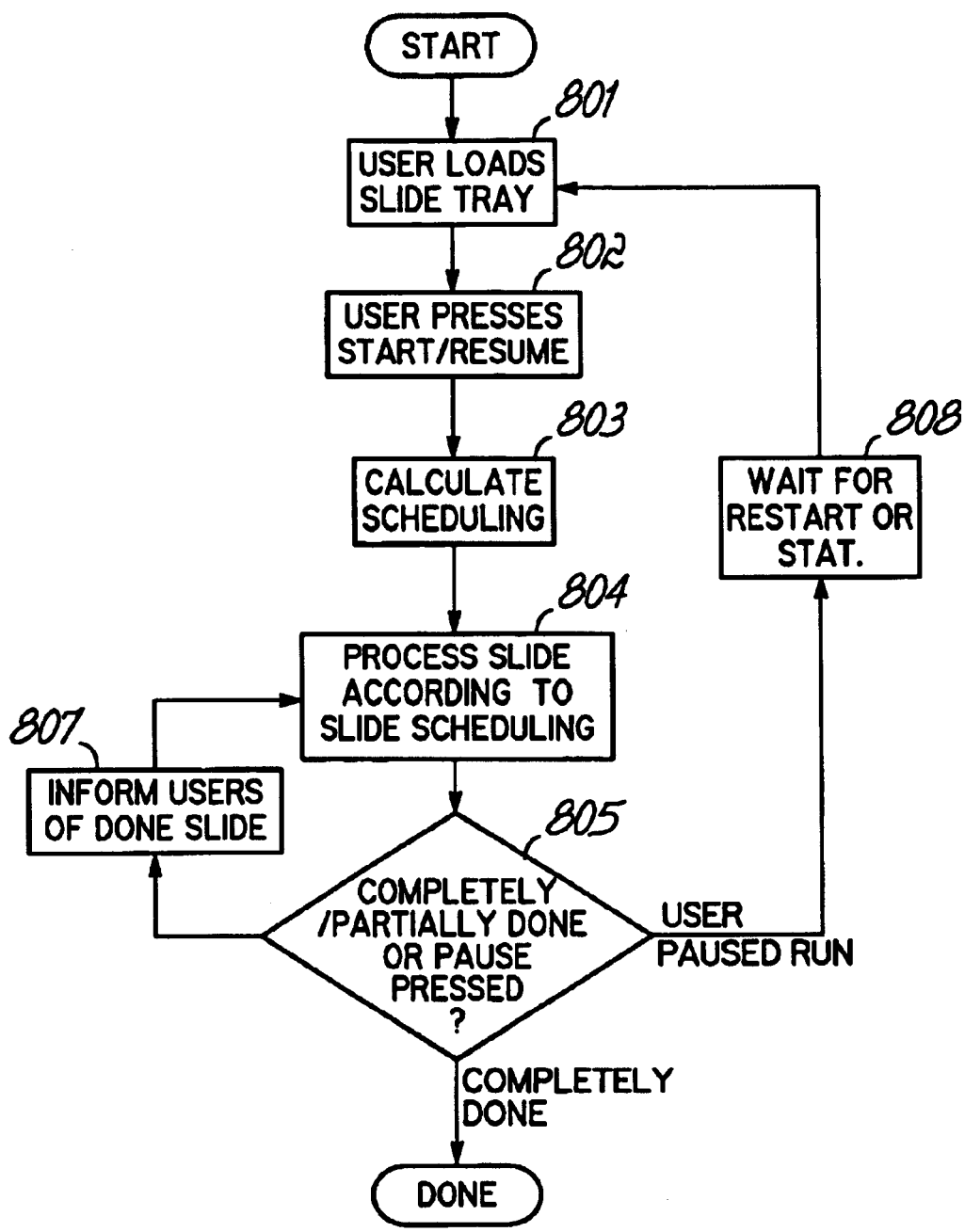
FIG. 8A illustrates a flow diagram of the general operation of the autostainer apparatus.

Once a user has loaded the autostaining apparatus, the user may start staining run. FIG. 8A illustrates the general procedure of operating the autostaining device. Referring to FIG. 8A, the user loads a slide/stain tray at step 801. The user then starts the apparatus by pressing the restart or stat button at step 802. The autostaining apparatus then examines all the slides to determine the slide protocols that must be performed at step 803. The system may compare a barcode sticker 420 on a slide with a barcode 411 on the cover 410 of an adjacent reagent pack to ensure that the proper reagent pack has been placed next to each slide. After examining all the slides and reagent packs, the system creates a staining schedule. Details on how the staining apparatus creates the staining schedule will be presented in the following section.

After calculating a staining schedule, the autostaining apparatus begins to process slides according to a created staining schedule. The system continues the staining operations until one of the conditions of step 805 are detected (or an error occurs). Specifically, step 805 determines if the staining run is completely done, the staining run is partially done, or if the user has pressed the pause button.

If the staining run is partially done, then the system proceeds to step 807 where the user is informed of the completed slide(s). The user may wish to remove those slides such that they can be examined.

If the user pressed the pause button, then the system temporarily ceases operation. The user may then load additional slide trays at step 801. The system remains paused as it waits for the user to press the restart or stat button. Once the user has pressed either the restart or stat button at step 802, the system proceeds to step 803 to create a new staining schedule. The system then resumes slide staining at step 804 using the new staining schedule.

Referring back to step 805, if the system is completely done with the staining run, then the system may cease operation. As shown in FIG. 8A, a user may continually remove completed slide trays and add new slide trays continually by only using the pause and restart/stat buttons. Thus, the staining apparatus may be in continuous operation all day long.

Slide Preparation Scheduling

Once the slide preparation protocols that need to be performed have been identified, the autostainer control program proceeds to calculate the most efficient dispensing pattern for performing the desired slide protocols.

Figure 8B:
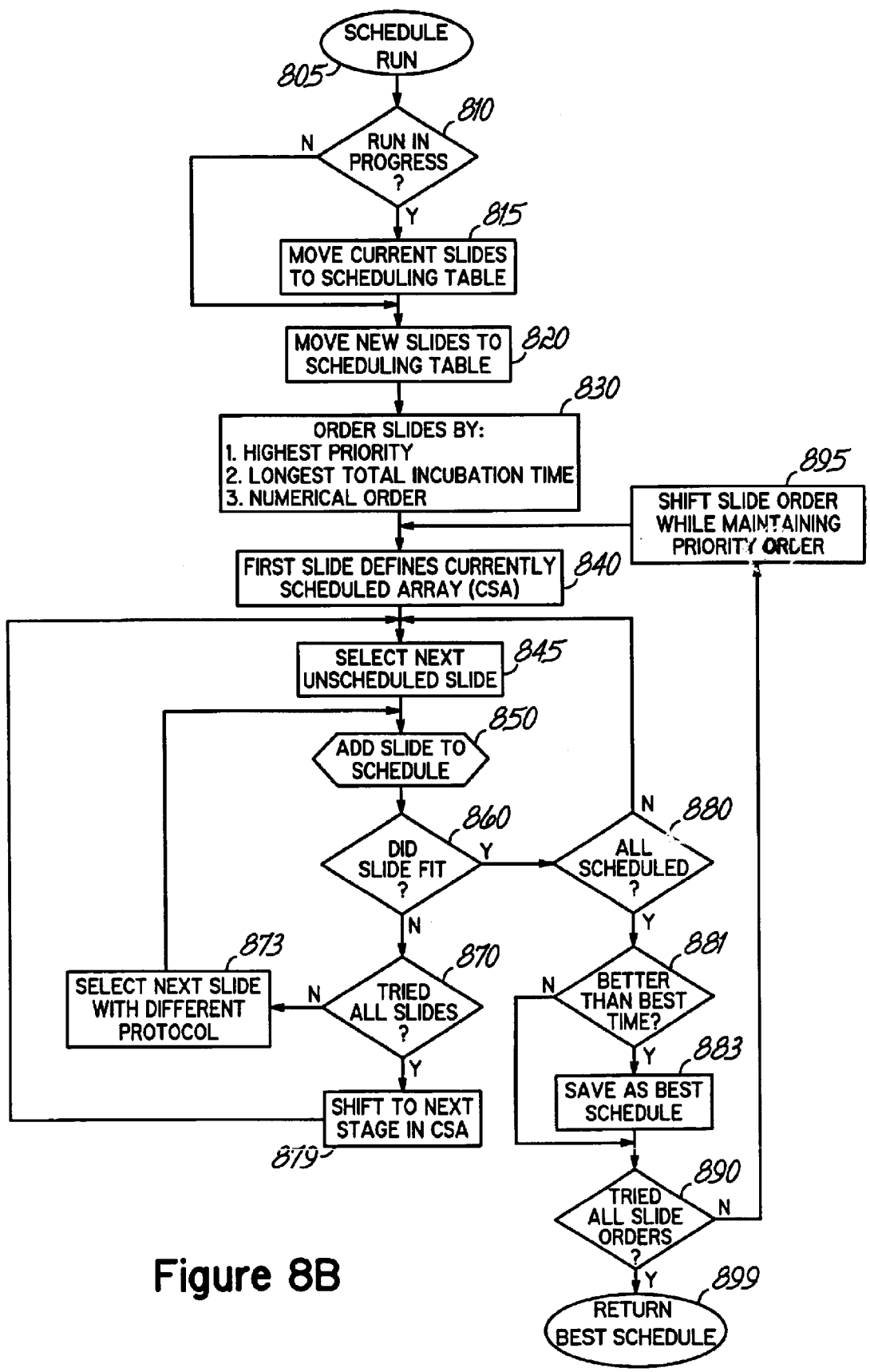
FIG. 8B illustrates a flow diagram summary of the slide protocol scheduling system of the autostainer control program.
Figure 9A:
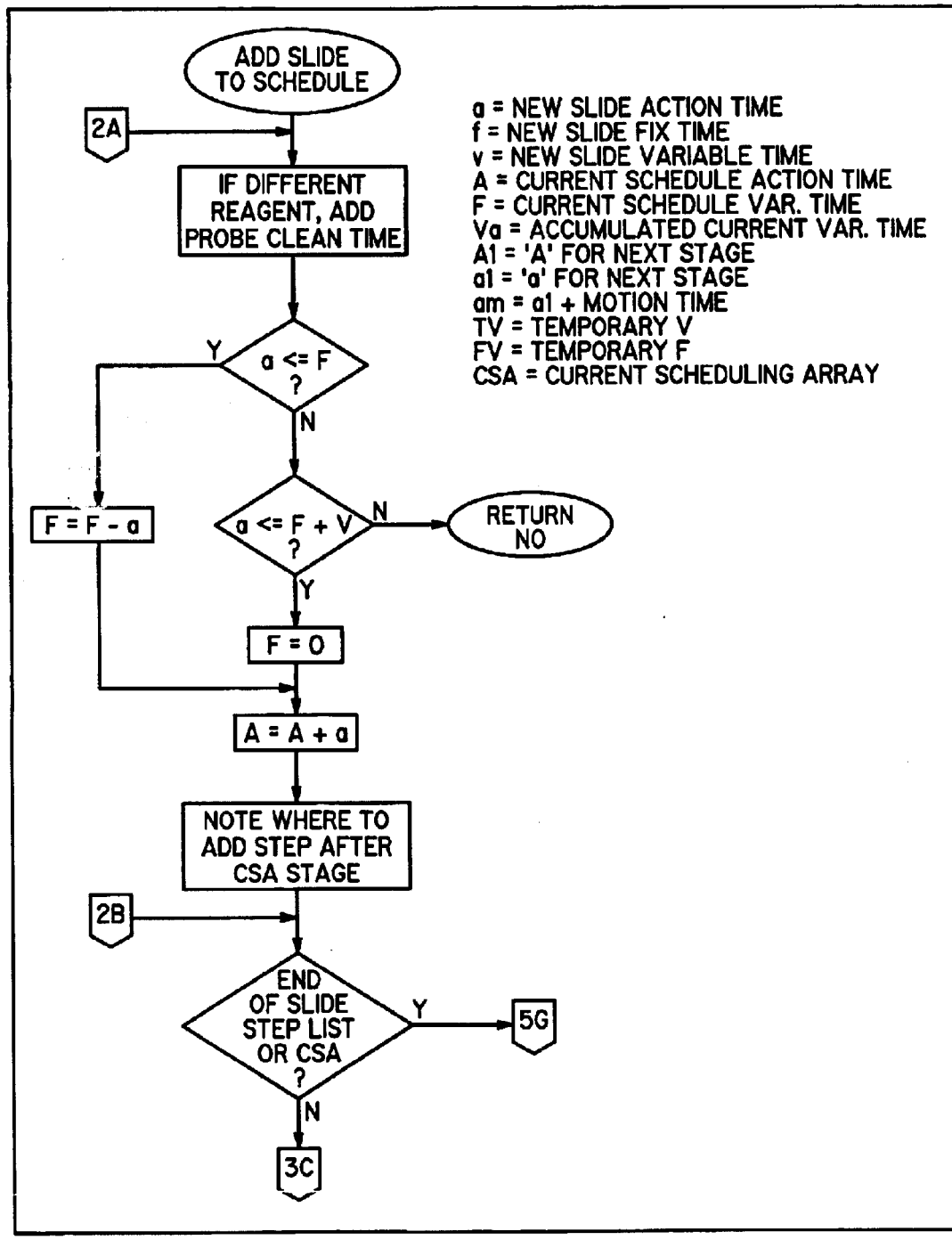
FIGS. 9a through 9d illustrate a flow diagram describing the details of adding a new slide to the Currently Scheduled Array (CSA).
Figure 9B:
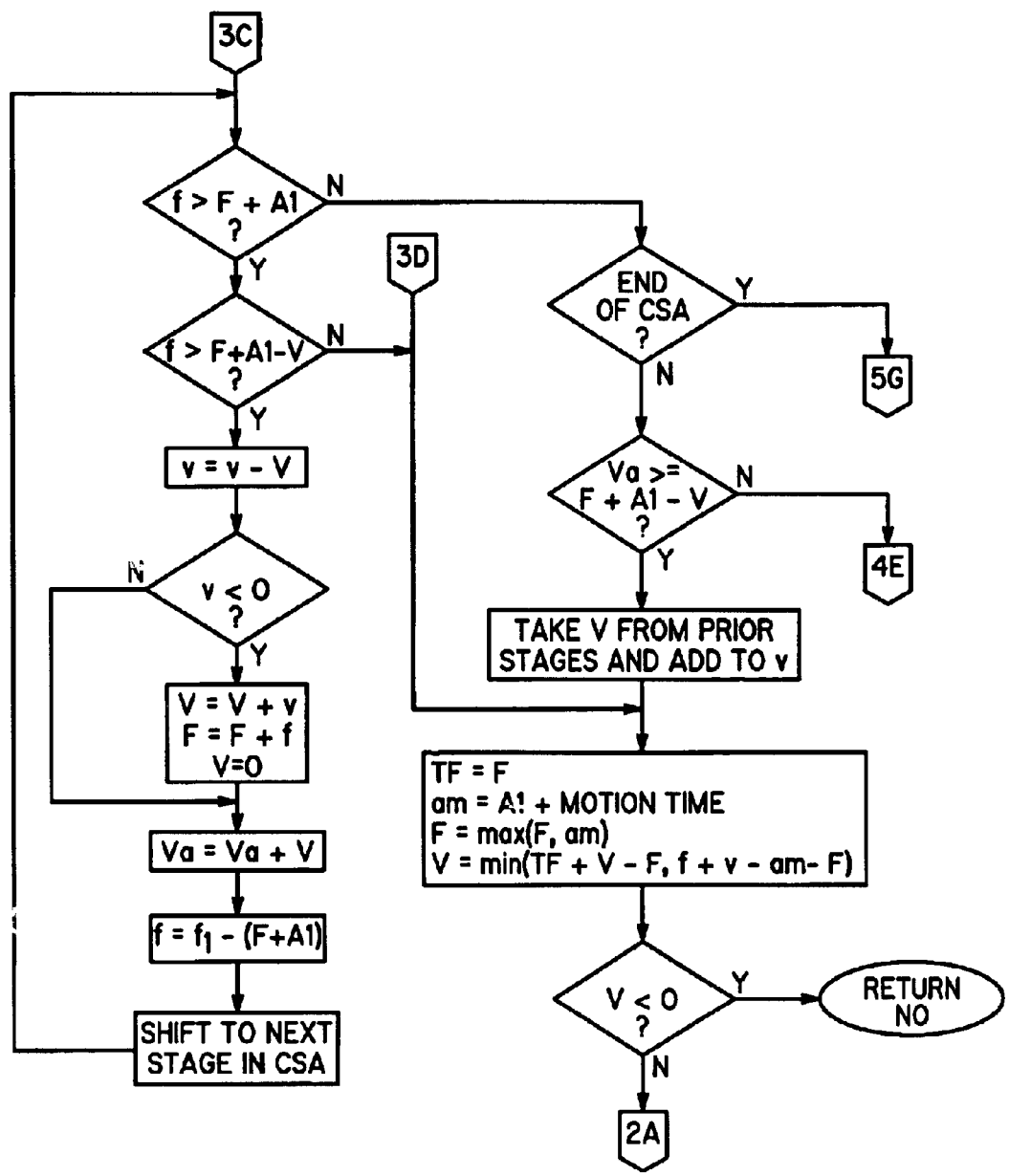
Figure 9C:
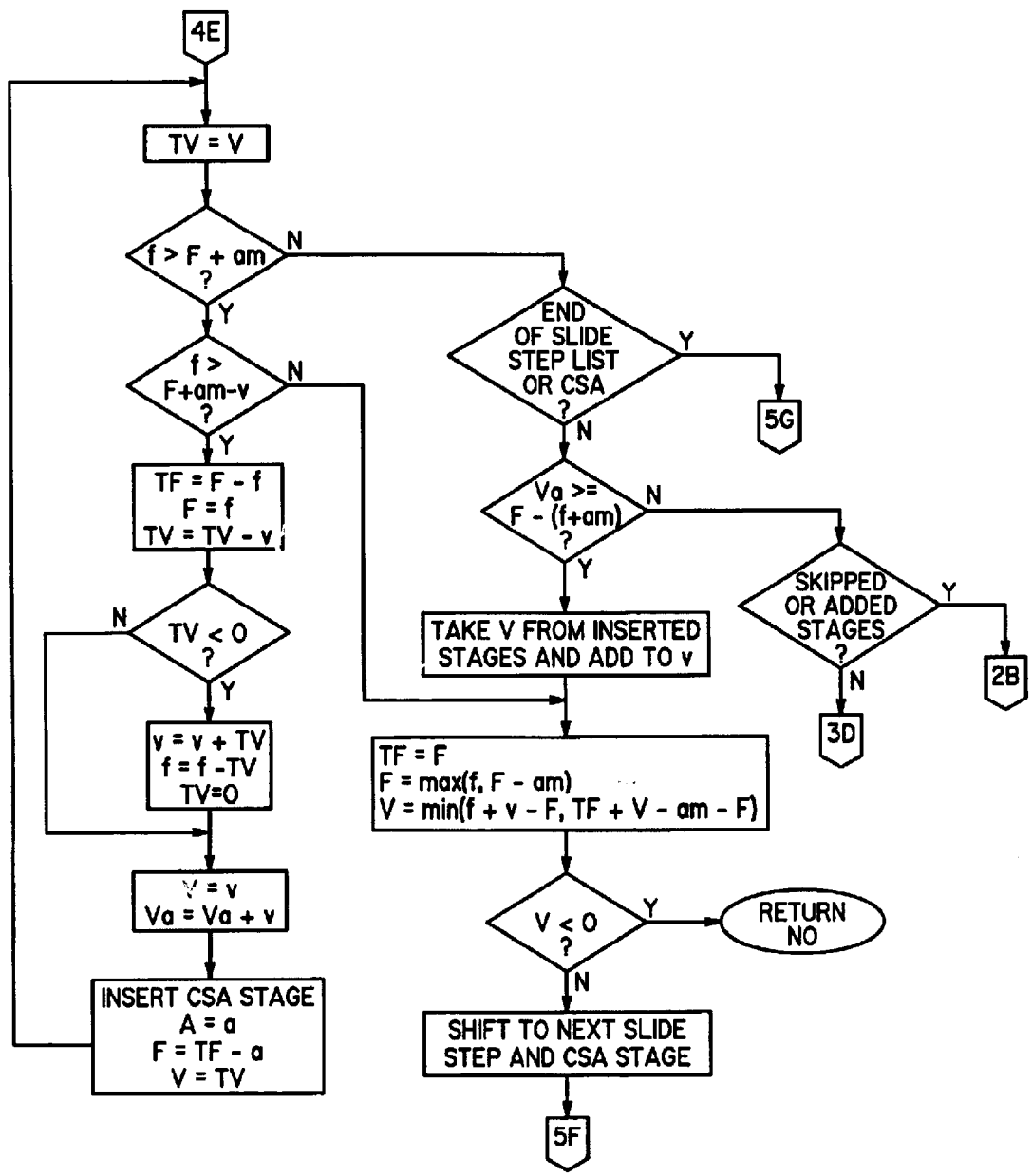
Figure 9D:
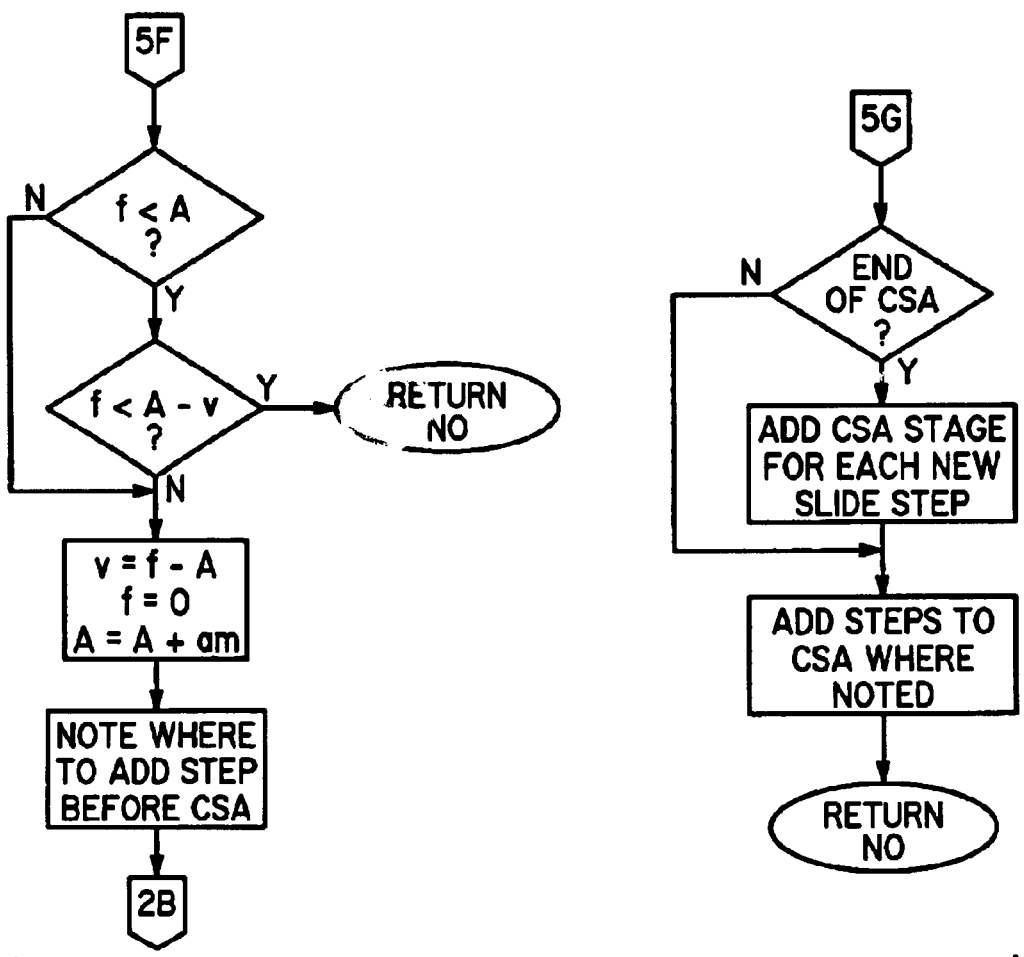

FIG. 8B illustrates a summary of how the autostainer control program calculates the most efficient dispensing pattern. Referring to FIG. 8B, at step 810 the autostainer control program first determines if a run was already in progress. If a run was already in progress, then the autostainer control program adds the current slides into a scheduling table at step 815. The scheduling table will be used to program the autostainer control program.

Next, at step 820, the autostainer control program has the z-head assembly scan all the slide positions to determine if any new slides have been added or any existing slides have been taken away. If a slide that had not yet completed its protocol was removed, the autostainer may inform the user of the error and ask if the user wishes to place the slide back into the autostainer. When one or more new slides have been added, the autostainer control program adds those slides into the current scheduling table as stated in step 820 of FIG. 8B. If the user designated the new slides as "STAT", then those newly added slides are given top priority.

After the autostainer control program has added the filled scheduling table, the autostainer control program proceeds to step 830 to begin automatic programming. At step 830, the autostainer control program first places the slides into a specific order. In one embodiment, the autostainer control program orders the slides using this order:

1. Highest priority slides (such as STAT slides).
2. Slides with the longest incubation time.
3. Numerical order.

The system then proceeds to re-order the slides using a well-defined method. FIG. 8B illustrates one possible method of ordering the slides. Initially, the first slide from the order of step 830 defines the currently scheduled array (CSA). The CSA defines a newly proposed slide order. At step 845, the method selects the next unscheduled slide from the scheduling table. That slide is then placed into the CSA as stated in step 850. At step 860, the method determines if the slide fit properly into the current stage of the CSA. The method of determining if a slide "fits" into the current stage of the CSA is fully defined in FIGS. 9*a* to 9*d*. If the slide did not fit, the method proceeds to step 870 to determine if the control program has tried to fit all the remaining unscheduled slides into the current stage. If there are unscheduled slides that the autostainer control program has not attempted to put into the current stage, then the method proceeds to step 873 to select an unscheduled slide with a different protocol. The autostainer control program then returns to step 850 to attempt to add that slide into the current stage.

If, at step 870, the autostainer control program is unable to fit any unscheduled slide into the current stage, then the autostainer control program move to the next stage of the current schedule array (CSA) as stated in step 879. The autostainer control program then proceeds back to step 845 to start placing slides into the new stage.

Referring back to step 860, after each new slide is added to the CSA, the autostainer control program determines if all the slides have been scheduled as stated in step 880. If all the slides have been scheduled, the autostainer control program determines if it has created a slide-processing schedule that is faster than the current best time. If the autostainer control program determines that it created a slide-processing schedule faster than the previous best time, then the autostainer control program saves the newly created schedule as the best schedule at step 883. At step 890, the autostainer control program determines if it has tried all the possible slide orders. If it has not, the autostainer control program proceeds to step 895 where the autostainer control program changes the slide order while maintaining the designated slide priority order. The autostainer control program then proceeds back to step 840 to test a new slide schedule. If, at step 890, the autostainer control program determines that it has tried every possible slide order (that maintains the slide priority order), the autostainer control program returns the best schedule.

The foregoing has described a method and apparatus for automatic tissue and cell preparation staining. It is contemplated that changes and modifications may be made by one of ordinary skill in the art, to the materials and arrangements of elements of the present invention without departing from the scope of the invention.

We claim:

1. A method for automated staining of specimen slides supported in a slide tray, the method comprising providing a reagent pack supportable in the slide tray and comprising reagents for staining a specimen slide, a first identifier and a second identifier, said first identifier and said second identifier identifying a staining protocol, removing said first identifier from said reagent pack, applying said first identifier to said specimen slide, reading said first identifier on said specimen slide and said second identifier on said reagent pack, and identifying the staining protocol in response to reading said first identifier and said second identifier.

2. The method of claim 1 further comprising:

initiating the staining protocol in response to said first identifier being the same as said second identifier, and not initiating the staining protocol when said first identifier is not the some as said second identifier.

3. The method of claim 1 further comprising scheduling staining protocols for a plurality of specimen slides.

4. The method of claim 1 further comprising placing the reagent pack in said slide tray adjacent said specimen slide.

5. The method of claim 1 wherein the first and second identifiers comprise the same information.

6. The method of claim 1 wherein the reagent pack comprises a set of wells for reagents for a staining protocol.

7. A method for automated staining of specimen slides comprising:

providing an apparatus comprising
at least one slide tray holding a first specimen slide and an associated accompanying specific reagent pack having reagents for processing said first specimen slide and identifiers for a first staining protocol,
an automatic staining head assembly operatively associated with said slide tray, said staining head assembly reading said identifiers, obtaining said reagents from said reagent pack and depositing said reagents on said first specimen slide,
a control system controlling said staining head assembly, and
a first input operative to cause said control system to pause said staining head assembly during processing, and
a second input operative to cause said control system to restart said staining head assembly after pausing, adding a second specimen slide to said apparatus during a processing of said first staining protocol for said first specimen slide, and initiating said control system to cause said staining head assembly to initiate processing of a second staining protocol for said second specimen slide.

8. The method of claim 7 further comprising initiating said first input prior to adding said second specimen slide.

9. The method of claim 7 wherein said identifiers comprise a barcode and said method further comprises initiating a staining protocol in response to reading said barcode with said staining head assembly.

10. The method of claim 7 wherein said second specimen slide requires initiating said second staining protocol prior to completion of said first staining protocol for said first specimen slide and the method further comprises initiating said second input to start an autocontrol program initiating said second staining protocol for said second specimen slide prior to completing said first staining protocol for said first specimen slide.

* * * * *

UNITED STATES PATENT AND TRADEMARK OFFICE
CERTIFICATE OF CORRECTION

PATENT NO. : 6,746,851 B1
DATED : June 8, 2004
INVENTOR(S) : Ken K. Tseung et al.

It is certified that error appears in the above-identified patent and that said Letters Patent is hereby corrected as shown below:

Title page,
Item [56], References Cited, OTHER PUBLICATIONS, reads "Biotex Solutions (1993), Techmate 500™ & Techmate 1000™ Automated Immunostaining System." and should read -- Biotek Solutions (1993), Techmate 500™ & Techmate 1000™ Automated Immunostaining System. --.

Column 8,
Lines 10-11, reads "... not initiating the staining protocol when said first identifier is not the some as said second identifier..." and should read -- not initiating the staining protocol when said first identifier is not the same as said second identifier ... --.

Signed and Sealed this

Seventeenth Day of May, 2005

JON W. DUDAS
*Director of the United States Patent and Trademark Office*